United States Patent [19]

Dieterich

[11] 4,225,532
[45] Sep. 30, 1980

[54] STABILIZED PREPARATIONS OF AROMATIC ISOCYANATOSULPHONIC ACIDS

[75] Inventor: Dieter Dieterich, Leverkusen, Fed. Rep. of Germany

[73] Assignee: Bayer Aktiengesellschaft, Leverkusen, Fed. Rep. of Germany

[21] Appl. No.: 12,251

[22] Filed: Feb. 15, 1979

[30] Foreign Application Priority Data

Feb. 22, 1978 [DE] Fed. Rep. of Germany ....... 2807458

[51] Int. Cl.² .......................................... C07C 119/048
[52] U.S. Cl. ....................... 260/453 SP; 260/453 AR
[58] Field of Search ................... 260/453 SP, 453 AR

[56] References Cited

U.S. PATENT DOCUMENTS

| | | | |
|---|---|---|---|
| 3,826,769 | 7/1974 | Carlson | 260/29.2 TN |
| 3,959,329 | 5/1976 | Dieterich | 260/453 AR |
| 4,143,062 | 3/1979 | Dieterich | 260/453 SP |

FOREIGN PATENT DOCUMENTS

| | | |
|---|---|---|
| 858467 | 3/1978 | Belgium . |
| 2227111 | 12/1973 | Fed. Rep. of Germany . |
| 2359619 | 6/1974 | Fed. Rep. of Germany . |
| 1383184 | 2/1975 | United Kingdom . |

*Primary Examiner*—Dolph H. Torrence
*Attorney, Agent, or Firm*—Gene Harsh; Lawrence S. Pope

[57] ABSTRACT

The present invention relates to a process for increasing the storage stability of solid aromatic isocyanatosulphonic acids by the addition of a substantially apolar, stabilizing agent which is inert towards isocyanate groups and sulphonic acid groups, which has a melting point in the region between about 27° and 250° C. and which, in the molten state, is a non-solvent for the isocyanatosulphonic acids. The present invention also relates to mixtures which are stable in storage and which may be in the form of a moist powder or a paste containing a mixture of solid, finely dispersed, aromatic isocyanatosulphonic acid and the substantially apolar, inert stabilizing agent mentioned above.

10 Claims, No Drawings

STABILIZED PREPARATIONS OF AROMATIC ISOCYANATOSULPHONIC ACIDS

BACKGROUND OF THE INVENTION

Sulphonic acids of aromatic di- and polyisocyanates are known. They are prepared simply by the reaction of the corresponding aromatic di- or polyisocyanates with sulphonating agents such as sulphur trioxide, adducts of sulphur trioxide, oleum, chlorosulphonic acid or sulphuric acid as described for example in German Published patent application No. 2,227,111 and its British concordance British Pat. No. 1,383,184; German Published patent application No. 2,359,619 and its U.S. concordance U.S. Pat. No. 3,959,329; and U.S. Pat. No. 3,826,769.

The sulphonation products may be obtained as solid, resinous or pulverulent substances or as solutions of the sulphonated isocyanates in unchanged starting isocyanate, depending on the isocyanate used and the degree of sulphonation.

Although there are no difficulties in handling liquid sulphonated polyisocyanates, the preparation, storage and use of solid pulverulent isocyanatosulphonic acids poses considerable problems.

The products are frequently obtained in such a finely divided state that they are difficult to separate and free from the liquid reaction medium. The dried products rise up as dust when poured into containers. Most importantly, dry powders produced by this method are not stable in storage. The melting and decomposition point rise during storage and the products become progressively more insoluble in organic solvents and in the polyesters, polyethers and polyols normally used for the preparation of polyurethanes.

Although insufficient stability in storage is a general problem of polyisocyanates and therefore well known in principle to the expert, in the case of solid pulverulent isocyanatosulphonic acids, the impairment of quality occurs after such a short time, e.g. in some cases after only a few days, that it makes the preparation of polyaddition products which can be used for practical purposes very difficult if not impossible.

On the other hand, there is a technical and commercial demand for the use of polyisocyanatosulphonic acids in polyaddition chemistry in addition to or instead of the usual diisocyanates and polyisocyanates because they are excellent starting materials for the production of hydrophilic polyurethanes, in particular polyurethanes which can be dispersed in water. Use of polyisocyanatosulphonic acids also appear to be particularly advantageous from the point of view of industrial hygiene or for physiological reasons because they have no vapor pressure and, on degradation, yield water-soluble amino sulphonic acids. The production of polyurethanes from sulphonated tolylene diisocyanate has hitherto been achieved either by sulphonating the prepolymer instead of the pure diisocyanate from which it is obtained as described in U.S. Pat. No. 3,826,769 or by preparing the isocyanatosulphonic acid only shortly before it was further processed to the polyurethane as described in U.S. Pat. No. 3,826,769. The first method has the disadvantage that it is restricted in the use of sulphonating agent, e.g. sulphur trioxide produces signs of decomposition in its action on polyether prepolymers. If sulphuric acid is used as sulphonating agent, chain lengthening with the formation of urea groups inevitably takes place at the same time. Furthermore, this method can only be used for sulphonating completely or partially free isocyanates but not products in the form of urethanes. This means that in an isocyanate prepolymer, only the isocyanate units present as end groups are sulphonated. The second method is not practicable on a commercial scale, because the manufacturer of a polyurethane cannot be expected first to carry out an isocyanate sulphonation.

It has also been proposed in U.S. Pat. No. 3,826,769 to dissolve the isocyanatosulphonic acids in an organic solvent, e.g. acetone, immediately after their preparation and then use them as solutions. This method also cannot be carried out on a commercial scale because a solution, for example of sulphonated tolylene diisocyanate in acetone, is not stable for more than a few hours at the most, after which the solution rapidly becomes cloudy and forms a precipitate.

It is, therefore, not surprising that solid isocyanatosulphonic acids have not so far become widely used in practice.

The problem, therefore, existed of preparing isocyanatosulphonic acids or stabilizing them so that they could be stored and used problem-free and their solubility in organic media would be maintained even after prolonged storage.

The present invention points a way to solving this problem. It has surprisingly been found that isocyanatosulphonic acids can be effectively stabilized by the addition of a substantially apolar, solid substance which is inert towards isocyanate groups and sulphuric acid groups and which has a melting point in the region between about 27° and 250° C. and which in the molten state is preferably a non-solvent for the aromatic isocyanatosulphonic acids, or, in other words, acts as a dispersing agent. The addition of only about 5% by weight of the solid dispersing agent is sufficient for stabilization, and the powder obtained does not fly up as dust.

SUMMARY OF THE INVENTION

The present invention relates to a process for increasing the stability in storage of finely dispersed, solid aromatic isocyanatosulphonic acids obtained by the sulphonation of aromatic isocyanates, characterized in that:

(a) sulphonation of the aromatic isocyanates is carried out in the presence of an inert liquid which is a non-solvent for the aromatic isocyanatosulphonic acids and consists either of a melt of an inert solid melting at a temperature above about 26° C. or a solution of such a solid in an inert solvent at a concentration of at least about 10% by weight, said solid being left at least partly in the sulphonation product after termination of the sulphonation reaction, or (b) solid, finely dispersed aromatic isocyanatosulphonic acids which have been prepared in the absence of a liquid of the type defined under (a) are mixed with such a liquid.

The present invention also relates to mixtures which are stable in storage and which may be in the form of a moist powder or a paste, containing (a) about 40 to 95% by weight of solid, finely dispersed, aromatic isocyanatosulphonic acids and (b) about 60 to 5% by weight of a substantially apolar solid substance which is inert towards isocyanate groups and sulphonic acid groups and has a melting point in the region between about 27° and 250° C. and which, when in the molten state, does not dissolve the aromatic isocyanatosulphonic acids mentioned under (a) at the melting point, characterized in that the solid substance mentioned under (b), optionally dissolved in inert liquids, envelop the particles of finely dispersed isocyanatosulphonic acids.

DETAILED DESCRIPTION OF THE INVENTION

The aromatic isocyanatosulphonic acids which are to be stabilized according to the invention may be any solid aromatic isocyanatosulphonic acids such as can be obtained in a finely divided form from the sulphonation of mono-, di- or polyisocyanates, e.g. the sulphonation products of phenylisocyanate; p-tolylisocyanate; p-chlorophenylisocyanate; p-nitrophenylisocyanate; p-methoxyphenylisocyanate; m-chlorophenylisocyanate; m-chloromethylphenylisocyanate; p-chloromethylphenylisocyanate; 4,4'-stilbene diisocyanate; 4,4'-dibenzyl diisocyanate; 3,3'- or 2,2'-dimethyl4,4'-diisocyanatodiphenylmethane; 2,5,2',5'-tetramethyl-4,4'-diisocyanatodiphenylmethane; 3,3'-dimethoxy-4,4'-diisocyanatodiphenylmethane; 3,3'-dichloro-4,4'-diisocyanatodiphenylmethane; 4,4'-diisocyanatodimethylmethane; 4,4'-diisocyanatodiphenylcyclohexylmethane; 4,4'-diisocyanatobenzophenone; 4,4'-diisocyanatodiphenylsulphone; 4,4'-diisocyanatodiphenylether, 4,4'-diisocyanato-3,3'-dibromodiphenylmethane, 4,4'-diisocyanato-3,3'-diethyldiphenylmethane; 4,4'-diisocyanato-diphenyl-ethylene-(1,2); 4,4'-diisocyanatodiphenylsulphide; 1,3- and 1,4-phenylene diisocyanate; 2,4- and 2,6-tolylene-diisocyanate and any mixtures of these isomers; diphenylmethane-2,4'- and/or 4,4'-diisocyanate; naphthylene-1,5-diisocyanate; triphenylmethane-4,4',4''-triisocyanate; polyphenyl-polymethylene polyisocyanates such as are obtained by aniline-formaldehyde condensation followed by phosgenation, as described, for example, in British Pat. Nos. 874,430 and 848,671; polyisocyanates with carbodiimide groups as described in German Pat. No. 1,092,007; the diisocyanates described in U.S. Pat. No. 3,492,330; polyisocyanates with allophanate groups as described, for example, in British Pat. No. 994,890, Belgian Pat. No. 761,626 and Dutch Published patent application No. 7,102,524; polyisocyanates with isocyanurate groups as described, for example, in German Pat. Nos. 1,022,789; 1,222,067 and 1,027,394 and in German Published patent applications No. 1,929,034 and No. 2,004,048; polyisocyanates with acylated urea groups according to German Pat. No. 1,230,778 and polyisocyanates with biuret groups as described, for example, in German Pat. No. 1,101,394; British Pat. No. 889,050 and French Pat. No. 7,017,514.

Pulverulent sulphonated di- and tri-isocyanates are preferred, in particular the mono- and disulphonic acids of the following isocyanates, which are generally in their dimeric form: 4,4'-diisocyanato-diphenylmethane; 2,4'-diisocyanato-diphenylmethane and, especially, 2,4-diisocyanatotoluene and 2,6-diisocyanatotoluene and mixtures of these isomers. The preparation of such pulverulent polyisocyanates has been described, for example, in U.S. Pat. No. 3,826,769 or German Published patent applications No. 2,524,476 and 2,615,876.

The pulverulent aromatic isocyanatosulphonic acids which are to be stabilized according to the invention are generally obtained by carrying out the sulphonation in excess isocyanate or in an inert organic dispersing agent such as dichloroethane or tetrachloroethane similarly to the methods described in the publications mentioned above. The particle size of the isocyanatosulphonic acids which are obtained as fine powders can easily be adjusted by suitable choice of the dispersing agent, the temperature at which sulphonation is carried out and the speed of stirring during sulphonation. The addition of surface active agents generally reduces the particle size obtained. The aromatic isocyanatosulphonic acids to be stabilized according to the invention generally have an average particle diameter of from about 0.0005 to 0.5 mm.

Liquid partially sulphonated aromatic polyisocyanate mixtures such as those described, for example, in German Published patent applications Nos. 2,227,111; 2,359,614 or 2,359,615 do not constitute isocyanatosulphonic acids which are to be stabilized according to the invention.

The mixtures according to the invention which are stable in storage contain, as a second, stabilizing component, inert organic substances which have a melting point in the region of from about 27° to 250° C., preferably from about 40° to 120° C. These substances are substantially apolar substances which are immiscible with water and which, in the molten state at their melting point, are non-solvents for the isocyanatosulphonic acids. These solid substances are present in the stable mixtures according to the invention in the form of solids which envelop the individual particles of the finely dispersed isocyanatosulphonic acids or in the form of a solution (in a suitable solvent) which wets the isocyanatosulphonic acids.

Examples of suitable solid substances melting in the region of from about 27° to 250° C., preferably from about 40° to 120° C., include paraffins, especially those melting in the region of from about 40° to 95° C., solid halogenated paraffins within the same melting range, solid ethers and esters of $C_{10}$–$C_{18}$ alcohols such as octadecylmethylether, didecylether, decylacetate or octadecylacetate, esters and amides of $C_1$–$C_{18}$ carboxylic acids such as stearic acidethyl ester or N,N-dimethylstearic-acid amide, naphthalene, durene, diphenylmethane, diphenyl, terphenyl and other solid aromatic hydrocarbons, diphenylether, diphenylsulphone, 4,4'-dichlorodiphenylsulphone, natural of synthetic waxes and especially solid polyesters, polyethers and derivatives thereof which are acylated at the ends of the chains. The following are specific examples: Polyethylene glycol adipate, polybutylene glycol adipate, polybutylene glycol succinate, polyethylene glycol sebacate, polybutylene glycol sebacate, polyhexanediol adipate, polyhexanediol oxalate, polyhexanediol succinate, polyhexanediol carbonate, polybutyleneglycol ether and polyhexanediol ether.

Mixed esters or ether esters of three or more of the usual glycollic acid and carboxylic acid components may, of course, also be used, provided their melting point is above about 26° C. It is preferable to use polyesters or polyethers which no longer contain reactive end groups and in which the hydroxyl groups originally present have been acylated, for example by reaction with an acylating agent such as acetic acid anhydride, or the carboxylic acid groups originally present have been esterified with monohydric alcohols, e.g. with methanol or ethanol.

Also particularly preferred are the di- or oligourethanes obtained from the above-mentioned polyesters or polyethers by reaction with monoisocyanates, to which diisocyanates may be added. Suitable monoisocyanates include, for example, methyl-, butyl-, phenyl-, 6-chlorohexyl- and, especially, stearyl-isocyanate.

The most suitable stabilizing agents are hydrophobic but only weakly polar substances which, although they do not dissolve isocyanatosulphonic acids, are not insoluble in the reaction mixture of isocyanatosulphonic acid and Zerewitinoff active components. In fact, the protective inert substance should dissolve when subsequently heated in the reaction mixture use, for example, for preparing polyurethanes from the stabilized isocyanatosulphonic acids according to the invention. For this reason, aliphatic hydrocarbons, particularly paraffins, are less preferred for the invention.

If the solid substances mentioned above have a melting point below about 150° C. and a sufficiently low viscosity in the molten state, they may be used alone. However, they are preferably used with inert solvents, and the resulting solution should contain at least about 10% of the solid substance according to the invention.

If the solid substances which are essential for the invention are used as solutions, the solvents used should be liquids which are non-solvents for the isocyanatosulphonic acids but dissolve these essential solid components. Furthermore, these liquids should be immiscible with water. Both liquids boiling above about 90° C., preferably above 110° C. and liquids boiling below about 90° C., preferably below about 60° C. may be used. When the higher boiling liquids are used as solvents for the essential solid substances according to the invention, they are generally left in the isocyanatosulphonic acids after these have been stabilized according to the invention, so that the substances according to the invention are obtained in the form of moist powders or pastes in which the isocyanatosulphonic acids are wetted with the solution of the essential solid according to the invention in the non-volatile solvent. If, on the other hand, the more volatile liquids are used as solvents for the essential solids according to the invention, these liquids generally evaporate after completion of the process according to the invention so that the mixtures according to the invention are obtained in the form of particles of isocyanatosulphonic acids enveloped with the essential substances according to the invention in the same way as when these solid substances are used as solvent-free melts.

It is also possible, for example, first to prepare a moist powder, using toluene as solvent (melting point 110° C.), and then to convert this into a dry powder according to the invention by a vacuum treatment. Examples of suitable liquids with boiling points above 90° C., preferably above 110° C., include heptane, octane, isooctane, nonane, decane, undecane, eicosane and mixtures of these hydrocarbons such as are obtained, for example, in commercial petroleum hydrocarbon and paraffin oil fractions, mineral spirits and mineral oils, e.g. solvent naphtha, cleaning petrol, petroleum, paraffin oil, polymerized olefines such as liquid polypropylene and polybutylene, tetraisobutene, methylcyclohexane, cyclododecane, dimethylcyclohexane, turpentine oil and decaline. Aromatic hydrocarbons such as toluene, o-, m- and p-xylene, commercial mixtures of aromatic compounds, cumene, pseudocumene, hemellitene, p-cymene, tetramethylbenzenes, diisopropylbenzenes, isododecylbenzene and tetraline are also suitable. Halogenated hydrocarbons, ketones, esters and ethers may also be used, provided they are sufficiently apolar, i.e. do not dissolve the isocyanatosulphonic acid. This is generally the case when the pure hydrocarbon component of the dispersing agent amounts to at least 70% by weight. The following are examples: Dibutylether, di-sec.-butylether, diisoamylether, methyl-isobutylketone, 4-heptanone, 5-methyl-3-heptanone, 2-undecanone, dinonylketone, dioctyl phthalate, trioctylphosphate and dioctyladipate.

Another group of suitable substances are the perchlorinated hydrocarbons such as highly chlorinated paraffins and chlorobenzene, dichlorobenzene and chlorocyclohexane.

Examples of suitable highly volatile liquids include petroleum ether, hexane, methylene chloride, chloroform, 1,2-dichloroethane, perchloroethane, acetone, methyl ethyl ketone, ethyl acetate and cyclohexane. Polar solvents such as the last mentioned ketones and esters may only be used as mixtures with sufficiently apolar solvents or solids in order to ensure that the isocyanatosulphonic acids which are to be stabilized do not dissolve in the solutions.

As will be clear from the examples already listed, the liquids and solid substances regarded as "inert" for the purpose of this invention should be understood to mean those which have no reactivity towards sulphonic acid groups and isocyanate groups. Liquids and solid substances used either as solutions or solvent-free melts which conform to these conditions and those already defined above are suitable for the particularly preferred embodiment (b) of the process according to the invention.

Liquids and solids in the form of solutions or melts used according to embodiment (a) of the process according to the invention must, in addition, be inert towards the sulphonating agents under the reaction conditions employed. Most of the liquids and solids mentioned as examples are inert towards sulphonating agents and may, therefore, be used as solvents for sulphonation according to the embodiment (a). Aromatic hydrocarbons, as is well known, can themselves be sulphonated. Their use is not subject to any restrictions if, according to embodiment (b), they are added to the reaction mixture after sulphonation has taken place. Their use as solvents for the isocyanates which are to be sulphonated, however, is possible only if they react considerably more slowly with sulphonating agents than do the isocyanates which are to be sulphonated or if slight sulphonation of these hydrocarbons is acceptable. Thus, for example, chlorobenzene and dichlorobenzene may be used as solvents for sulphonation, whereas toluene, xylene and cumene are preferably added after sulphonation. When preparing isocyanatopolysulphonic acids (derivatives containing more than one sulphonic acid group per molecule of the starting isocyanate used for sulphonation), it must be remembered that disulphonation proceeds much more slowly and with greater difficulty than monosulphonation. For these cases, therefore, only solvents or solids which are inert towards sulphur trioxide should be used for sulphonation. In the case of the aforesaid polysulphonic acid, moreover, the stabilization according to the invention proceeds independently of the nature of the stabilizing agent used according to the invention and preferably only after sulphonation and after removal of excess sulphonating agent according to embodiment (b).

The process according to the invention for the stabilization of isocyanatosulphonic acids may be carried out according to two variations:

Sulphonation of the isocyanate may be carried out, for example, as described in the literature cited above but the liquid which is an essential feature of the invention (solvent-free melt or solution of the solid substance) is added to the isocyanate before or during its sulphonation. After completion of the sulphonation reaction, a part of the additive used may be removed, for example by filtration or by suction filtration under vacuum. The only essential condition in this variation of the process in that the stabilizing inert solid which is essential to the invention should be left in the sulphonation product in a quantity conforming to the proportions of the components in the mixtures according to the invention.

Sulphonation may also be carried out, for example as described in the literature cited above, in the absence of stabilizers according to the invention and the product obtained, which may still be moist and contains a residual amount of auxiliary solvent such as dichloroethane or a residual amount of unsulphonated liquid starting isocyanate, is then mixed with the dispersing agent which is essential to the invention. The important condition is that the sulphonated isocyanate should be completely enveloped or penetrated by the dispersing agent according to the invention as far as possible immediately after its preparation but without being dissolved in it.

The mixtures according to the invention are dry powders, moist powders or pastes, depending on the quantity of auxiliary liquid present in them.

The quantity of the solid substance essential to the invention, i.e., in the first mentioned variation, the solid left in the mixture, is generally calculated to produce mixtures containing from about 40 to 95% by weight, preferably from about 60 to 90% by weight, of aromatic isocyanatosulphonic acids and from about 60 to .5% by weight, preferably from about 10 to 40% by weight of the stabilizing solid which is essential to the invention. The average particle diameter of the finely dispersed isocyanatosulphonic acid is from about 0.5 to 500 microns.

The stabilizing preparations according to the invention may also contain additives to increase the stabilizing effect or produce additional stabilizing effects such as resistance to yellowing. Apart from the liquids mentioned above, these include the well known light protective agents such as sterically hindered phenols, UV absorbents, the usual unsulphonated polyisocyanates, in particular aliphatic polyisocyanates with a low vapor pressure, organopolysiloxanes and chlorofluorinated hydrocarbon oils. The stabilized preparations are stable under conditions of storage and transport and are suitable for the preparation of various types of polyurethanes such as elastomers, foams, coatings, molded products and adhesives. While hydrocarbons such as octane, toluene or xylene evaporate during or after preparation or application of the polyurethane, high boiling substances such as phosphates, phthalates or polychloroparaffins are retained in the finished polyurethane as plasticizers or micro droplets.

The stabilized isocyanatosulphonic acids remain soluble in polyesters, polyethers and tetrahydrofuran even after prolonged storage. Polyurethanes produced from them are free from inhomogeneities and cloudiness. One particular advantage of the dry powders, pastes and moist powders according to this invention is their reduced need for liquid components for the preparation of reaction mixtures and their lower viscosity in a given formulation. Furthermore, the quantity of air inevitably introduced into the mixture is considerably less and the mixtures are relatively or completely free from foam, bubbles and give rise to more homogeneous reaction mixtures.

The special advantage of the isocyanatosulphonic acids stabilized according to the invention is to be seen in the fact that the products can be handled and transported as dry powders without the solubility and reactivity of the products of the process being impaired.

Another advantage lies in the possibility of enveloping the pulverulent isocyanatosulphonic acids with thinner or thicker layers as desired, whereby the velocity of the reaction in a reaction medium can be controlled. For example, it is possible to distribute the compositions according to the invention in aqueous media without an immediate reaction with the water occurring. The dripping time of highly reactive systems can in this way be adjusted as desired.

EXAMPLES

EXAMPLE 1

1914 g (11 mol) of tolylene diisocyanate (isomeric mixture 2,4:2,6=80:20) are reacted with 335 g (4.2 mol) of sulphur trioxide at 23° to 30° C. for about 20 hours with stirring. A thick suspension of dimeric tolylene diisocyanate monosulphonic acid in tolylene diisocyanate is formed. Sulphur trioxide is released from heated 65% oleum with a slow stream of nitrogen and passed over the surface of the stirred isocyanate as a gas diluted with nitrogen. The resulting suspension is diluted with 500 ml of toluene and suction filtered and the solid residue is twice stirred up with 500 ml of a 20% by weight solution of diphenyl in toluene and suction filtered. The product, moist with tolulene, is filled into containers. Yield 1310 g, toluene and diphenyl content 26%, dry substance 970 g corresponding to 91% of the theoretical amount.

The product is a slightly moist powder which is very easy to handle without forming dust. It is easily filled into containers or refilled, does not cake and does not stick to the spatula.

EXAMPLE 2

300 g of the moist powder obtained according to Example 1 is dried at 35° C. in a vacuum drying cupboard and the dry powder is filled into containers. Yield 246 g. The product is dry and free flowing and does not form dust. A sample of product which has been stored for 6 weeks is soluble and forms a clear solution in tetrahydrofuran.

EXAMPLE 3

The procedure is the same as in Example 1 but pure molten diphenylether at 35° C. is used instead of the 20% solution of diphenyl in toluene. The suspension of dimeric tolylene diisocyanatomonosulphonic acid in diphenyl ether is filtered with sharp suction on a suction filter heated to 40° C., and the filter cake is then broken up under conditions of cooling. The product remains soluble in tetrahydrofuran even after prolonged storage in air.

EXAMPLE 4

The procedure is the same in Example 1 but the 20% solution of diphenyl in toluene is replaced by a 10% solution of the reaction product of 1 mol of polyethylene glycol adipate (hydroxyl end groups, molecular weight, $\overline{M}n$, 2000) with 2 mol of stearyl isocyanate in methylene chloride. The resulting suspension is suction filtered and the filter cake is dried in air at room temperature. The dry powder is still soluble in tetrahydrofuran after 4 weeks' storage, whereas a comparison sample treated in the same way, but prepared from dichloromethane alone, forms a cloudy solution in tetrahydrofuran.

EXAMPLE 5

The procedure is the same as in Example 1 but using a 25% solution of the reaction product of 1 mol of polytetrahydrofuran (molecular weight, $\overline{M}n$, 3000) with 2 mol of chlorohexyl isocyanate. Processing and solubility of the product are the same as in Example 4. When the dry product is introduced into water, evolution of gas sets in only after a few minutes.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as is set forth in the claims.

What is claimed is:

1. A process for increasing the stability in storage of finely dispersed solid aromatic isocyanatosulphonic acids obtained by the sulphonation of aromatic isocyanates comprising sulphonating the aromatic isocyanate in the presence of a liquid which is inert towards isocyanate groups and sulphonic acid groups, which is a non-solvent for the aromatic isocyanatosulphonic acids and which is either (a) a melt of a solid stabilizing agent which is inert towards isocyanate groups and sulphonic acid groups and which has a melting point above about 26° C. or
    (b) at least a 10% by weight solution of the solid stabilizing agent of (a) in a solvent which is inert towards isocyanatosulphonic acids, characterized in that said solid stabilizing agent remains in the sulphonation product after termination of the sulphonation reaction in an amount between about 5% and 60% by weight, based on the weight of the sulphonation product.

2. A process for increasing the stability in storage of finely dispersed solid aromatic isocyanatosulphonic acids obtained by the sulphonation of aromatic isocyanates comprising mixing a solid, finely dispersed aromatic isocyanatosulphonic acid with a liquid which is inert towards isocyanate groups and sulphonic acid groups, which is a non-solvent for the aromatic isocyanatosulphonic acid and which is either (a) a melt of a solid, stabilizing agent which is inert towards isocyanate groups and sulphonic acid groups and which has a melting point above about 26° C. or
    (b) at least a 10% by weight solution of said solid stabilizing agent in a solvent which is inert towards isocyanatosulphonic acids, characterized in that said solid stabilizing agent is present in the resultant mixture in an amount between about 5% and 60% by weight, based on the weight of the mixture.

3. The process of either claims 1 or 2, wherein the solid stabilizing agent has a melting point between about 27° and 250° C.

4. A process for increasing the stability in storage of finely dispersed solid aromatic isocyanatosulphonic acids obtained by sulphonation of aromatic isocyanates, characterized in that (a) sulphonation of the aromatic isocyanates is carried out in the presence of an inert liquid which is a non-solvent for the aromatic isocyanatosulphonic acids and which is either a melt of an inert solid which melts about 26° C. or an at least 10% by weight solution of such a solid in an inert solvent, characterized in that said solid is at least partly left in the sulphonation product after termination of the sulphonation reaction, or
    (b) solid, finely dispersed aromatic isocyanatosulphonic acids prepared in the absence of a liquid of the type defined under (a) are mixed with such a liquid.

5. A storage stable mixture comprising
    (a) about 40–95% by weight of solid, finely dispersed, aromatic isocyanatosulphonic acids and
    (b) about 60–5% by weight of a solid stabilizing agent which is inert towards isocyanate groups and sulphonic acid groups and has a melting point between about 27° and 250° C.,
characterized in that the solid stabilizing agent completely envelops the particles of the finely dispersed isocyanatosulphonic acids.

6. The storage stable mixtures of claim 5, wherein the solid stabilizing agents have a melting point between about 40° and 120° C.

7. The storage stable mixtures of either claims 5 or 6, wherein the solid stabilizing agents are substantially apolar.

8. The storage stable mixtures of either claims 5 or 6, wherein the solid stabilizing agents are dissolved in a solvent which is a non-solvent for the isocyanatosulphonic acids.

9. The storage stable mixtures of claim 8, wherein the mixture is in the form of a moist powder or paste.

10. A mixture which is stable in storage and which is optionally in the form of a moist powder or paste, containing
    (a) about 40–95% by weight of solid, finely dispersed, aromatic isocyanatosulphonic acids and
    (b) about 60–5% by weight of a substantially apolar solid substance which is inert towards isocyanate groups and sulphonic acid groups, has a melting point in the region of from about 27° to 250° C. and is a non-solvent for the aromatic isocyanatosulphonic acid mentioned under (a), characterized in that
the solid substance mentioned under (b), optionally dissolved in inert liquids, envelops the particles of the finely dispersed isocyanatosulphonic acids.

* * * * *